United States Patent [19]

West et al.

[11] 4,133,821

[45] Jan. 9, 1979

[54] ALKYLIDENEDIQUINOCYCLOPROPANES AND DIARYLCYCLOPROPENES AND METHOD FOR PREPARATION

[75] Inventors: Robert C. West, Madison, Wis.; Douglas E. Beyer, Midland, Mich.; Koichi Komatsu, Kyoto, Japan

[73] Assignee: Wisconsin Alumni Research Foundation, Madison, Wis.

[21] Appl. No.: 777,836

[22] Filed: Mar. 15, 1977

[51] Int. Cl.² .................. C07C 49/62; C07C 49/72
[52] U.S. Cl. .................. 260/396 N; 252/500; 252/501; 260/465 D; 260/465 F; 260/590 C; 260/590 FA; 560/59; 568/721
[58] Field of Search .................. 260/396 N; 252/500, 252/501

[56] References Cited

U.S. PATENT DOCUMENTS 4,052,209  4/1977  Huffman et al. .................. 96/1.5

OTHER PUBLICATIONS

West et al., J.A.C.S., (Jan. 1970), 92:1, pp. 149–167.

*Primary Examiner*—Vivian Garner
*Attorney, Agent, or Firm*—McDougall, Hersh & Scott

[57] ABSTRACT

Alkylidenediquinocyclopropanes and diarylcyclopropenes and the preparation of the former by oxidation of the latter and which are characterized by low energy electronic absorption, pronounced dichroism and characteristic specular reflectance.

11 Claims, No Drawings

ALKYLIDENEDIQUINOCYCLOPROPANES AND DIARYLCYCLOPROPENES AND METHOD FOR PREPARATION

The Government has rights in this invention pursuant to Grant No. MPS-74-01345 and IPA No. 0001 awarded by the National Science Foundation.

This invention relates to alkylidenediquinocyclopropanes and their precursor diarylcyclopropenes.

A new class of highly conjugated compounds, referred to as quinocyclopropanes, has been reported several years ago by West and Zecher, *J. Amer. Chem. Soc.* 92, 155 (1970). The compounds represent brilliant blue-purple dyes (max 770 mm) with semi-conductive properties. Also known is the diquinocyclopropanone in which a carbonyl group replaces one of the quinoid groups in the corresponding triquinocyclopropane. West, Zecher, Koster and Eggerding, *J. Org. Chem.* 40 2295 (1975). The diquinocyclopropanone is prepared by excitation of a bis(hydroxyaryl) cyclopropenone.

By reaction of a bis(hydroxyaryl) cyclopropenone with active methylene compounds, it has been found possible to prepare a series of methylene cyclopropene derivatives 6 (a-f) which undergo oxidation to a new family of stable alkylidenediquinocyclopropanes 5 (a-f) in accordance with an object of this invention.

The latter compounds are deeply colored crystalline solids, royal blue or blue-purple in solution, and like the diquinocyclopropanes, have intense low-energy electronic absorption. These compounds are characterized, in addition, by pronounced dichroism and a characteristic specular reflectance. Compounds herein identified as 5a, 5b and 5c appear metallic gold in reflected light while compounds 5d, 5e and 5f reflect reddish brown, resembling metallic copper.

The diarylcyclopropanes (6) and corresponding alkylidenediquinocyclopropanes (5) are represented by the following formulae:

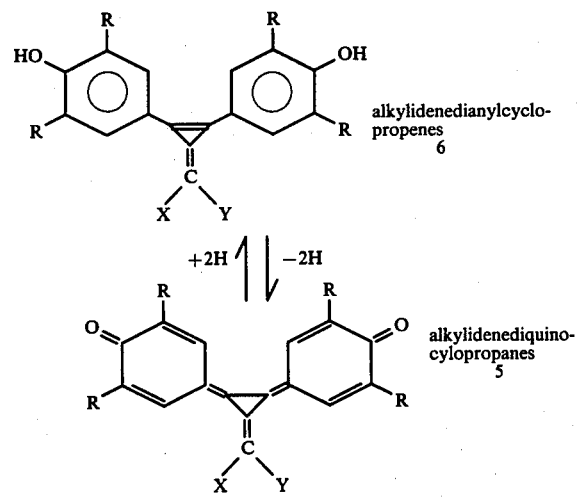

where X and Y are electronegative groups which can be the same or different. X and Y are represented by the following groups:

| X and/or Y preferred | X and/or Y general |
|---|---|
| (a) NC | (a') NC |
| (b) COOEt | (b') COOR |
| (c) MeC⟍O | (c') RC⟍O |

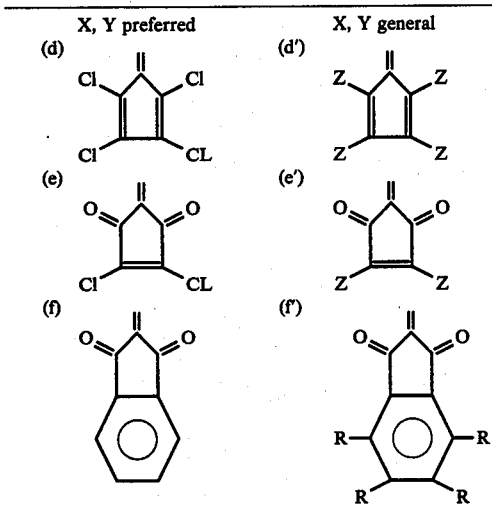

in which Z is a halogen, preferably chlorine, and in which each R may be the same or different and is representative of such groups as hydrogen, a $C_1$–$C_{18}$ alkyl, cycloalkyl or alicyclic group such as methyl, ethyl, propyl, cyclopropyl, butyl, isobutyl, pentyl to octadecyl, and preferably t-butyl or isopropyl; an aryl or alkaryl group such as toluyl, benzyl, naphthyl, anthracyl, or a heterocyclic group. The remainder of any valences in the ring structures are occupied by hydrogen.

The remainder of the specific will be devoted to examples for the preparation of representative compounds in the two groups and their identification.

In general, the alkylidene diarylcyclopropenes 6 were prepared by the reaction of diarylcyclopropenones of the general structural formula shown below with methylene compounds, i.e., malenonitrile, ethyl cyanoacetate, 1,2-dichlorocyclopentene-3,5-dione, giving the condensed product in yields of 17-70%.

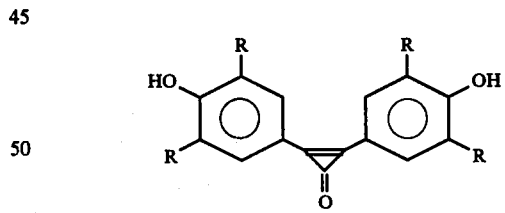

This reaction is supposed to proceed through the acetoxyclyclopropenine ion formed by the action of acetic anhydride upon the cyclopropenone, followed by condensation with active methylene substrates. When this condensation is carried out with 1,2-Bis(3,5-di'-tert-butyl-4-hydroxyphenyl)cyclopropenone 4, the intermediate diarylacetoxycyclopropenium ion is probably stabilized by the p-hydroxyl groups, and this may account for the acceleration of the reaction.

Only with 1,2,3,4-tetrachlorocyclopentadiene was it necessary to carry out the reaction under milder conditions (in methanol), using the silylated compound 7 to avoid reaction of the hydroxyl groups.

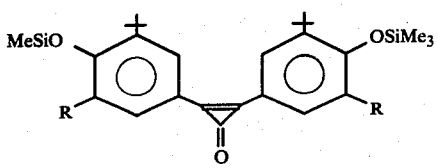

7

The condensed products 6a-f are all pale to brilliant yellow crystals exhibiting spectral properties consistent with the assigned structures. In the ir spectrum they all possess a sharp band at ~3600 cm$^{-1}$ (hindered OH) and a weak band at ~1830 cm$^{-1}$ (cyclopropene double bond [4a]). In the nmr spectra the aryl protons appear at relatively low field, consistent with dipolar character in these compounds with the cyclopropene ring bearing some positive charge. The spectrum of 6b shows quite different shielding for the ortho protons in the two aryl rings ($\delta$8.18 and $\delta$8.52), indicating restricted rotation around the exocyclic double bond. From comparison with the chemical shift of the aryl protons in 6e ($\delta$8.52) and 6f ($\delta$8.69), the one appearing at lower field ($\delta$8.52) is assigned to the aryl proton on the same side as —CO$_2$Et. This rather large low-field shift found in 6b, 6e and 6f is probably due to strong deshielding caused by the diamagnetic anisotropy of the carbonyl group which is directed toward the cyclopropene ring. This is consistent with the remarkable low-energy shift of the >C=O stretching band (1620 cm$^{-1}$) in the ir spectrum, indicating a large contribution by the polarized structure. Likewise, in compounds 6e and 6f, the enhanced dipolar character caused by the para-dihydroxyl group is apparent from the lower energy carbonyl stretching band (ir) and the lower field shift for ortho protons (nmr) than those reported for the corresponding diphenyl compounds.

The uv-visible spectra of all the compounds 6, except 6d, exhibited distinctive bathochromic shifts upon changing the solvent from methanol (polar) to cyclohexane (nonpolar). This is again in accordance with a large contribution of the ionic dipolar structure to the ground state. Only for 6d did the uv-visible maxima remain essentially the same in methanol, benzene and cyclohexane, suggesting that there is little change in dipole moment between the ground and excited states.

Dianion Formation. Methanol solutions of 6a-f were titrated spectrophotometrically with aqueous NaOH. For all the compounds, two molar equivalents of NaOH were required for complete change of the spectrum and only one set of isosbestic points was observed as shown in Table 1 for the representative case 6c. These results indicate that the neutral compounds 6 are converted directly to the dianions, the monoanions being unstable. This transformation was completely reversible as was indicated by regeneration of 6 by addition of aqueous HCl after each titration.

The alkylidenediquinocyclopropanes 5 were prepared by a two phase oxidation of the diarylcyclopropene 6 in chloroform with an alkaline solution of potassium ferrocyanide, to give excellent yields of 5.

For compound 6a oxidation was also effected by lead dioxide, lead tetracetate and N-chlorosuccinimide with triethylamine in organic solvents. Two-electron oxidation of the dianion of 6a (as the sodium salt) with iodine gave a quantitative yield of 5a as well.

Electronic Spectra. The long wavelength maxima of compounds 5 lie between 600 and 675 nm (Table 1). The characteristic metallic appearance of these compounds in the solid state is associated with their reflectance spectra which show even lower energy absorption than the solution spectra except for 5d (Table 1). Among compounds 5 the most remarkable spectrum was obtained from 5a and 5c, which exhibit extremely low-energy absorptions at 870 nm and 925 nm, respectively, as shown in Table 2 for 5a.

Ir and Nmr Spectra. Structures of the alkylidenediquinocyclopropanes 5 were confirmed by their ir and nmr spectra. In the ir spectrum, they all have a strong band near 1600 cm$^{-1}$ characteristic of related quinonoid compounds,[1,3,16] while the OH and cyclopropene absorptions are absent. In the nmr spectra, the tert-butyl groups (of 5a, 5d, 5e and 5f) and the quinoidal ortho protons each appear as two different sets of signals. This clearly indicates the existence of exocyclic double bonds which prohibit rotation of quinoidal rings. The rigid planar structure of 5 is especially apparent in compounds 5e and 5f from the remarkable low-field shift ($\delta$8.83 and $\delta$9.10, respectively) of the quinoidal protons (which are closer to carbonyl groups). The geometry of these protons, fixed very close to the carbonyl groups, apparently causes even larger low-field shifts than in compounds 6e and 6f.

Radical Anions. Tetrahydrofuran solutions of 5a-f were electrolytically reduced and examined by esr spectroscopy. Strong esr signals appeared with minimal current and remained unchanged for several hours at room temperature even after the current was cut off, indicating remarkably high stability for the anion radicals (5a-f) in solution. The anion radicals of 5c, 5d, 5e and 5f exhibited very similar five-line esr patterns with relative intensities 1:4:6:4:1, indicating splitting by four nearly equivalent ortho protons, as shown in Table 1 for 5e. The observed coupling constants and those predicted by the method of McLachlan, Mol. Phys., 3, 233 (1960) using Huckel molecular orbitals (vide infra) and a value of 1.0 for $\lambda$ are shown in Table 2. Thus, the introduction of these electron-withdrawing and $\pi$-conjugative substituents (c-f) into the diquinocyclopropane ring system seems to have little spin-delocalizing effect. In 5f no splitting by the aryl protons of the indanedione nucleus was observed, in good agreement with the calculated results (by the Huckel molecular orbital method) which indicate almost zero (0.0002-0.0003) spin densities for the corresponding carbon atoms.

For cyano compounds 5a and 5b the esr spectra were more complicated because of interaction of the unpaired electron with the nitrogen atoms. Compound 5a exhibited an incompletely resolved 14 line spectrum, which matched reasonably well with a computer simulated spectrum assuming coupling with four equivalent protons ($a_H = 0.59$ G) and two equivalent nitrogens ($a_N = 0.96$ G). The $a_H$ value for the quinoidal protons is slightly smaller than for 5c-f, consistent with somewhat greater spin delocalization by the dicyanomethylene group than by the other alkylidene substituents. For 5b, a six- (or possibly eight-) line pattern was observed, but we have been unable to interpret this spectrum to data and it is possible that it is due to a decomposition product rather than to the anion radical 5b.

The data and materials in the following specific examples were developed in accordance with the following procedures:

Melting points are uncorrected. Spectra were recorded by means of the following instruments: Infra red, Perkin-Elmer - 237; proton nmr, Jeol MH-100;

ultra violet — visible and reflectant, Cary 14; mass spectra, CHC Type 21-103C; esr, Varian 4502-13.

As for the materials, Bis(3,5-di-tert-butyl-4-hydroxyphenyl)cyclopropenone 4 was prepared as has been reported.[3] 1,2,3,4-tetrachlorocyclopentadiene and 1,2-dichlorocyclopentene-3,5-dione were prepared according to the method of Roedig and Horning.[21] Bis(3,5-di-tert-butyl-4-trimethylsiloxyphenyl) cyclopropenone was prepared from 4 by the following method. A stirred mixture of 2.58 g (5.58 mmol) of 4 and 2.50 g (12.3 mmole) of bis(trimethylsylyl)acetamide (Aldrich) in 6.5 ml of acetonitrile which had been freshly distilled over $P_2O_5$ was heated at 60° for 10 min. Immediately after 4 went into solution a dense white precipitate formed, which was filtered, washed with dry acetonitrile and dried under vacuum to give 3.05 (90.2%) of the bis(-siloxyaryl)cyclopropenone ad a white powder; mp 180–183° (dec); ir (KBr) 2960–2860(m), 1830(sh), 1815(s), 1600(s), 1460(w), 1430(m), 1400(a), 1360(m), 1330(s), 1260(s), 1250–1235 (br,s), 1200(m), 1120(m), 920(m), 895(m), 875(s), 850(s), 780(w), 650 cm$^{-1}$ (w); nmr (CCl$_4$) δ0.47(s, 18HO), 1.52 (s, 36HO), 7.86(s, 4H).

All the other materials were commercially available.

EXAMPLE 1

1,2-Bis(3,5-di-tert-butyl-4-hydroxyphenyl)-3-dicyanomethylene cyclopropene (6a):

A mixture of 1.00 g (2.17 mmol) of bis(3,5-di-tert-butyl-4-hydroxyphenyl)cyclopropenone 4, 0.29 g (4.3 mmol) of malonitrile and 0.02 g of β-alanine in 3.0 ml of freshly distilled acetic anhydride was heated to reflux with stirring for 20 min. A white precipitate formed in the reddish brown solution. The mixture was cooled to room temperature, and the precipitate was collected by filtration and recrystallized from benzene to give 0.62 g (56%) of 6a as pale yellow needles; mp 280–281°, (dec); ir (KBr) 3560(m), 2960–2860(m), 2213(m), 2197(m), 1850(w), 1595(m), 1490(s), 1470(m), 1450(w), 1410(s), 1370(s), 1360(s), 1310(s), 1255(s), 1240(m), 1200(w), 1100(m), 1025(w), 925(w), 900(w), 890(sh), 885(w), 780(w), 760(w), 675(2), 655(w), 595 cm$^{-1}$(w); nmr (CDCl$_3$) δ1.52(s, 36HO), 5.98(s,2H), 7.91(s,4H); uv-visible $\lambda_{max}$ (methanol) 233 nm (log 4.40), 242(4.34), 252(4.29), 299(4.62), 313(4.57), 368(4.54), 396(sh) (4.44); only the longest wavelength absorptions will be shown for the uv-visible spectrum in nonpolar solvents, $\lambda_{max}$ (benzene) 381 nm, 400(sh); mass spectrum m/e 510.32500 (calc. 510.32462); Anal. Calcd. for $C_{34}H_{42}N_2O_2$: C, 79.95; H, 8.29; N, 5.49. Found: C, 80.03; H, 8.32; N, 5.43.

EXAMPLE 2

1,2-Bis(3,5-di-tert-butyl-4-hydroxyphenyl)-3-carboethoxycyanomethylenecyclopropene (6b):

A mixture of 3.70 g (8.00 mmol) of 4, 1.81 g (16.0 mmol) of ethylcyanoacetate, and 0.02 g of β-alanine in 12.0 ml of freshly distilled acetic anhydride was refuxed for 8 hr with stirring under nitrogen atmosphere. To the resulting red solution was added 100 ml of benzene and the mixture was washed twice with 200 ml of water and twice with 200 ml of 10% NaHCO$_3$. After drying (MgSO$_4$), the organic solution was evaporated in vacuo to give 4.6 g of crude mixture which was then chromatographed over a column which was packed with neutral alumina (100 g) at the bottom and with silica gel (115 g) at the top. Elution with 5% ethereal benzene afforded 1.39 g (31.1%) of crude 6b. Recrystallization from hexane-chloroform gave pale yellow crystals; mp 254–255° (dec); ir (KB4) 3600(s), 3090(w), 2960–2860(m), 2203(m), 1840(w), 1690(s), 1590(m), 1490(s), 1450(sh), 1410(2), 1390(w), 1365(s), 1325(m), 1275 (m-s), 1255(m), 1240(m), 1200(w), 1155(m), 1115(w), 1080(s), 890(w), 810(w), 760(m), 640 cm$^{-1}$(w); nmr (CDCl$_3$) δ1.35(t, 3HO), 1.55(s, 36H), 4.35(q,2H), 5.96(s, 1H), 6.02 (s, 1H), 8.18 (s, 2HO), 8.52(s, 2H); uv-visible $\lambda_{max}$ (methanol) 233 nm (log E 4.29), 240(sh) (4.26), 250(4.18), 302(4.43), 317(4.50), 368(4.42), 388(sh) (4.29), $\lambda_{max}$ (cyclohexane) 384 nm, 404(sh); Anal. Calcd for $C_{36}H_{47}NO_4$: C, 77.52; H, 8.49; N, 251. Found: C, 77.43; H, 8.47; N, 2.46.

From successive elution with 50% ethereal benzene, 1.25 g (33.8%) of 4 was recovered.

EXAMPLE 3

1,2-Bis(3,5-di-tert-butyl-4-hydroxyphenyl)-3-diacetylmethylene cyclopropene (6c):

A mixture of 4.6 g (10.0 mmol) of 4, 4.00 g (40.0 mmol) of 2,4-pentanedione, and 0.1 g of β-alanine in 15.0 ml of acetic anhydride was refluxed for 10 hr and worked up in the same manner as above. The crude product was dissolved in 12 ml of benzene and stirred with 2.0 ml of conc HClO$_4$ at 0°. The resulting white precipitate was filtered, washed with benzene, and dried under vacuum to give 1,2-bis-(3,5-di-tert-butyl-4-hydroxyphenyl)-3-(2'-hydroxy-4'-oxo-2'-penten-3-yl)-cyclopropenium perchlorate as a white powder which slowly decomposes at 160–180°; ir (KBr) 3600–3370(br), 2960–2840(m), 1580(m), 1550(w), 1540(w), 1440(w), 1385(s), 1360(s), 1360(s), 1315(w), 1255(m), 1230(w), 1195(w), 1100(br,s), 1020(w), 930(w), 880 cm$^{-1}$ (w). The perchlorate salt of the cyclopiopenium ion was dissolved in 10 ml chloroform and 0.5 ml of triethylamine was added with stirring. The resulting yellow solution was washed with water, dried (MgSO$_4$) and evaporated in vacuo to give 0.79 g (15) of 6c as pale yellow crystals after recrystallization from benzene; mp 230–231° (dec); ir (KBr) 3620(m), 2960–2850(m), 1820(w), 1620(s), 1590(s), 1445(m), 1385(s), 1355(s), 1320(sh), 1305(m), 1260(s), 1235(m), 1190(m), 1075(s), 1020(m), 950(m), 940(sh), 915(w), 890(m), 780(m), 720(w), 680(w), 625 cm$^{-1}$(w); mnr (CDCl$_3$) δ1.50(s, 36H), 2.50(s, 6H), 5.84(s, 2H), 7.96 (s, 4H); uv-vixible, $\lambda_{max}$ (methanol) 239 nm (log λ 4.34), 272(4.28), 324(4.52), 360(sh) (4.39), $\lambda_{max}$ (cyclohexane) 364 nm; Anal. Calcd for $C_{36}H_{48}O_4$: C, 79.37; H, 8.88. Found: C, 79.18; H, 8.91.

EXAMPLE 4

1,2-Bis(3,5-di-tert-butyl-4-hydroxyphenyl)-3-(2',3',4',5'-tetrachloro-2', 4'cyclopentadien-1'-ylidene)cyclopropene (6d):

A mixture of 6.06 g (10.0 mmol) of bis(3,5-di-tert-butyl-4-trimethylsiloxyphenyl)-cyclopropenone and 4.08 g (20.0 mmol) of 1,2,3,4-tetrachloro-1,3-cyclopentadiene in 140 ml of anhydrous methanol was stirred at 45±5° for 1 hr to give a yellow solution and then kept at room temperature for 20 hr. The resulting yellow precipitate was filtered, washed with hexane, and dried under vacuum to afford 0.70 g (8.8%) of 1,2-bis(3,5-di-tert-butyl-4-trimethylsiloxyphenyl)-3-(2',3',4',5'-tetrachloro-2',4'-cyclopentadien-1'-ylidene)cyclopropene as a bright yellow powder; mp > 230° (no clear mp); ir (KBr) 2960–2840(m), 1825(w-m), 1585(m), 1500(s), 1445(w-m), 1400(s), 1385(m), 1360(sh), 1340(s), 1290(s), 1260(sh), 1235(s), 1195(w), 1115(w), 1005(m), 920(w), 885 (m), 870(s), 835(m), 775(w), 750(w), 650 cm$^{-1}$ (w); nmr (CDCl$_3$) 0.44(s, 18H), 1.46(s, 36H), 8.16(s,4H).

The filtrate was concentrated to ca 70 ml by rotary evaporation and then let stand overnight at $-20°$. The resulting yellow crystals (4.30 g) were chromatographed over 100 g of silica gel. Elution with benzene afforded 1.32 g (16.7%) of 6d as yellow needles after recrystallization from hexanebenzene; mp 240–241° (dec); ir (KBr) 3600(m), 2970–2850(m), 1830(w), 1590(m), 1500(s), 1445(w), 1410(s), 1355 (m), 1290(s), 1250(w), 1233(m), 1150(m), 1110(w), 1010(m), 915(w), 880(w), 770(w), 675 cm$^{-1}$ (w); nmr (CDCl$_3$) δ 1.52(s, 36HO), 5.92(s, 2H), 8.07 (s,4H); uv-visible $\lambda_{max}$ (methanol) 244 nm (lot є4.14), 288(sh) (4.11), 312(4.19), 360(4.68); $\lambda_{max}$ (cyclohexane) 360 nm, $\lambda_{max}$ (benzene) 362 nm; mass spectrum m/e 646.19388 (calc 646.19366); Anal. Calcd for C$_{36}$H$_{42}$Cl$_4$O$_2$: C, 66.67; H, 6.53; Cl, 21.87. Found: C, 66.55; H, 6.59; Cl, 21.79.

Successive elution with 30% ethereal benzene gave 2.95 g (63.9%) of 4.

EXAMPLE 5

1,2-Bis(3,5-di-tert-butyl-4-hydroxyphenyl)-3-(3',4'-dichloro-3'-cyclopenten-2',5'-dion-1'-ylidene)cyclopropene (6e):

A mixture of 1.39 g (3.00 mmol) of 4 and 0.80 g (4.9 mmol) of 1,2-dichloro-1-cyclopenten-3,5-dione in 3.6 ml of acetic anhydride was refluxed for 10 min and then cooled at $-20°$ overnight. The resulting precipitate was filtered, washed with ether, and dried under vacuum to give 1.18 g (64.7%) of 6e as yellow powder after recrystallization from CCl$_4$-CHCl$_3$; mp >290°; ir (KBr) 3600(m), 2950–2860(m), 1835(w), 1670(sh), 1655(s), 1590(m), 1490(s), 1410(s), 1360(s), 1325(s), 1295(w), 1255(m), 1240(s), 1195(w), 1160(m), 1137(m), 1120(m), 1100(m), 1055(m), 930(w), 920(w), 880(w), 855(w), 810(m), 770(w), 690(w), 650 cm$^{-1}$(w); nmr (CDCL$_3$) δ 1.56(s, 36H), 5.96 (s, 2H), 8.52 (s, 4H); uv-visible $\lambda_{max}$(methanol) 241 nm (log є 4.56), 278 (4.01), 330(4.64), 362(4.49), 382(sh) (4.41), $\lambda_{max}$(cyclohexane) 393 nm; mass spectrum m/e 608.24600 (calc 608,24578); Anal. Calcd for C$_{36}$H$_{42}$Cl$_4$O$_2$: C, 70.92; H, 6.95; Cl, 11.63. Found: C, 70.86; H, 6.80;, Cl, 11.88.

1,2-Bis(3,5-di-tert-butyl-4-hydroxyphenyl)-3-(indane-1',3'-dion-2'-ylidene)cyclopropene (6f):

A mixture of 3.00 g (6.50 mmol) of 4, 1.90 g (13.0 mmol) of 1,3-indanedione, and 0.02 g of β-alanine in 8.0 ml of acetic anhydride was refluxed for 2 hr. The resulting precipitate was filtered; washed with ether to give 2.82 g (73.5%) of 6f as pale pink colored crystals after recrystallization from chloroform; mp 295–296° (dec); ir (KR4) 3596(s), 2950–2850(m), 1834(m), 1653(s), 1480(s), 1409(m), 1353(m), 1236(s), 1197(w), 1141(s), 1121(w), 1020(w), 922(m), 875(m), 810(w), 771)w), 749(w), 730(m), 672(w), 644 cm$^{-1}$(w); nmr (CDCl$_3$) δ 1.60(s, 36H0), 5.94(s, 2H), 7.70(m, 4H), 8.69 (s, 4H); uv-visible $\lambda_{max}$(methanol) 210 nm (log є 4.61), 232(4.62), 285(4.20), 298(4.21), 364(4.73), $\lambda_{max}$(cyclohexane) 372 nm; Anal. Calcd for C$_{40}$H$_{46}$O$_4$: C, 81.32; H, 7.85. Found: C, 81.23; H, 7.82.

EXAMPLE 6

1,2-Bis(3,5-di-tert-butyl-4-oxo-2,5-cyclohexadiene-1-ylidene)-3-dicyanomethylenecyclopropane (5a):

A solution of 1.00 g (3.04 mmol) of potassium ferricyanide in 20 ml of 1N KOH solution was added to a solution of 0.51 g (1.0 mmol) of 6a in 20 ml of chloroform. The deep blue two-phase mixture was stirred vigorously at room temperature for 1 hr under a nitrogen atmosphere. The organic layer was separated, washed with water, dried (MgSO$_4$) and evaporated in vacuo to give 0.50 g (98%) of 5a as golden plates after recrystallization from hexane; mp 210–215° (dec); ir (KBr) 2960–2860(m), 2227(w), 2217(w), 1753(m), 1600(s), 1525(w), 1510(w), 1470(s), 1360(m), 1345(m), 1260(w), 1115(s), 1020(w), 950(w), 910(m), 830 cm$^{-1}$(w); nmr (CDCl$_3$) δ 1.34(s, 18H), 1.38(s, 18H0); 7.45(d,J = 2Hz, 2H), 7.71 (d, J = 2Hz, 2H); uv-visible, $\lambda_{max}$ (benzene) 319(sh) (3.77), 345(sh) (3.90), 364(4.03), 387(sh) (4.01), 415(sh) (3.88), 498 (sh) (3.96), 548(sh) (4.40), 587(4.79), 609 (4.80), 640(sh) (4.25); mass spectrumm/e 508.31003 (calcd 508.30897); Anal. Calcd for C$_{34}$H$_{40}$N$_2$O$_2$: C, 80.27; H, 7.93; N, 5.51. Found: C, 80.40; H, 8.09; N, 5.48.

EXAMPLE 7

1,2-Bis(3,5-di-tert-butyl-4-oxo-2,5-cyclohexadien-1-ylidene)-3-carboethoxycyanomethylenecyclopropane (5b):

In exactly the same manner as above 0.30 g (0.54 mmol) of 6b was oxidized with excess K$_3$Fe(CN)$_6$ to give 0.30 g (100%) of 5b as dark purple plates with golden reflection after recrystallization from hexanebenzene; mp 230–231° (dec); ir (KB4) 2960–2860(m), 2215(w), 1743(m), 1700(m), 1585(s), 1530(w), 1480(w), 1455(m), 1390(w), 1360(m), 1250(s), 1175(w), 1120(w), 1090(s), 1070(m), 1060(m), 935 (w), 905(w), 820(w), 770 cm$^{-1}$(w); nmr (CDCl$_3$) δ 1.40(S, 36H), 1.48 (t,3H), 4.46(q, 2H), 7.56 (br,s,2H), 8.06(d,1H0), 8.86 (d, 1H); uv-visible $\lambda_{max}$ (benzene) 291 nm (log є 4.24), 362 (4.01), 550(sh)(4.45), 591(4.82), 609(4.80); Anal. Calcd for C$_{36}$H$_{45}$NO$_4$: C, 77.80; H, 8.16; N, 2.52. Found: C, 77.70; H, 8.21; N, 2.46.

EXAMPLE 8

1,2-Bis(3,5-di-tert-butyl-4-oxo-2,5-cyclohexadien-1-ylidene)-3-diacetylmethylenecyclopropane (5c)

In the same way, K$_3$Fe(CN)$_6$ oxidation of 0.37 g (0.68 mmol) of 6c afforded 0.36 g (97%) of 5c as dark purple plates with golden reflection after recrystallization from hexane; mp 180–190° (dec); ir (KBr) 2960–2840(m), 1730(m), 1685(s), 1645(m), 1590(s), 1540(w), 1500(w), 1480(m), 1450(m), 1390(w), 1360(s), 1255(m), 1200(m), 1090(s), 1025(m), 930(m), 895(m), 820(w), 750(s), 630 cm$^{-1}$(w); nmr (CDCl$_3$) δ 1.40(s, 36H), 2.52(s, 6H), 7.54(d, J = 2Hz, 2H), 7.86(d, J = 2Hz, 2H); uv-visible $\lambda_{max}$ (benzene 296 nm (log є4.13), 357(4.03), 557(sh) (4.46), 608(4.70); Anal, Calcd for C$_{36}$H$_{46}$O$_4$: C, 79.66; H, 8.54, Found: C, 79.39; H, 8.50.

EXAMPLE 9

1,2-Bis(3,5-di-tert-butyl-4-oxo-2,5-cyclohexadien-1-ylidene)-3-(2',3',4',5'-tetrachloro-2',4'-cyclopentadien-140-ylidene)cyclopropane (5d):

Similarly oxidation of 0.58 g (0.73 mmol) of 6d with excess K$_3$Ke(CN)$_6$ gave 0.57 g (99%) of 5d as dark purple crystals with reddish copper-like reflectance after recrystallization from hexane; mp 200 -210° (dec); ir (KBr) 2960–2840(m), 1700(m), 1590(s), 1520 (w), 1465(m), 1450(m), 1390(w), 1360(m), 1270(s), 1250(m), 1165(m), 1120(w), 1090(s), 1005(w), 895(m), 820(w), 650 cm$^{-1}$(w); nmr (CDCl$_3$) δ 1.34(s, 18H), 1.37(s, 18H), 7.48(d, J = 2Hz, 2H), 7.94(d, J = 2Hz, 2H); uv-visible $\lambda_{max}$(benzene) 313 nm (log ε 4.16), 357(4.14), 390(4.10), 672(4.60); Anal. Calcd for $C_{36}H_{40}Cl_4O_2$: C, 66.88; H, 6.24; Cl, 21.94. Found: C, 66.64; H , 6.40; Cl, 21.75.

EXAMPLE 10

1,2-Bis(3,5-di-tert-butyl-4-oxo-2,5-cyclohexadien-1-ylidene)-3-(3',4'-dichloro-3'-cyclopenten-2',5'-dion-1'-ylidene) cyclopane (5e)

In the same way oxidation of 0.46 g (0.76 mmol) of 6e gave 0.45 g (98R) of 5e as dark purple crystals with reddish reflectance after recrystallization from hexane-benzene; mp 255°–260° (dec); ir (KBr) 2960–2840(w), 1745(m), 1860(s), 1575(s), 1470(w), 1440(w), 1380(w), 1355(m), 1250(w), 1220(m), 1195(m), 1120(m), 1080(w), 1010(w), 930(w), 900(m), 810(w), 750 cm$^{-1}$(w); nmr (CDCl$_3$) δ 1.39(s, 18HO), 1.45 (s, 18H), 7.52(d, J = 2Hz, 2H), 8.83(d, J = 2Hz, 2H); uv-visible $\lambda_{max}$ (benzene) 296 nm (log ε 4.33), 372(4.06), 390(4.05), 420(sh)(3.95), 550(sh)(4.36), 600(4.77), 621(4.75); Anal. Calcd for $C_{36}H_{40}Cl_2O_4$: C, 71.16; Y, 664; Cl, 11.67. Found: C, 71.09; H, 6.50; Cl, 11.81.

EXAMPLE 11

1,2-Bis(3,5-di-tert-butyl-4-oxo-2,5-cyclohexadien-1-ylidene)-3-(indene-1',3'-dion-2'-ylidene)cyclopropane (5f):

Similarly, oxidation of 0.59 g (1.00 mmol) of 6f with excess $K_3Fe(CN)_6$ afforded 0.58g (99%) of 5f as dark reddish purple crystals after recrystallization from hexane-chloroform; mp 236 –238° (dec); ir (KBr) 2960–2860(m), 1750(m), 1677(s), 1580(br,s), 1525(w), 1480(m), 1450(m), 1390(w), 1350(m), 1325(m), 1240(s), 1200(w), 1160(m), 1125(m), 1113(w), 1090(m), 1055(w), 1015(w), 940(w), 910(s), 890(w), 820(m), 740(s), 685(w), 650 cm$^{-1}$(w); nmr (CDCl$_3$) δ 1.40(s, 18H), 1.50(s, 18H), 7.52(d, J = 2Hz, 2H), 7.87(m, 4H), 9.10(d, J = 2Hz, 2H); uv-visible$\lambda_{max}$ benzene 290 nm (log ε 4.30), 307(4.28), 372(4.19), 394(4.15), 423(4.03), 563(sh)(4.42), 610(4.84), 627(sh)(4.80), 668(sh)(4.34); Anal. Calcd for $C_{40}H_{44}O_4$: C, 81.60; H, 7.53. Found: C, 81.73; H, 7.60.

SPECTROPHOTOMETRIC TITRATION OF 6

The base titration of compounds 6a–6f was carried out by the following general method: to a well-stirred solution of 0.020 mmol of 6 in 100 ml of spectrograde methanol was added 0.10 N aqueous NaOH in 0.10 ml aliquots by the use of micropipet. The uv-visible spectrum was recorded after each addition of the base and the sample solution was returned to the main branch. No spectral change (beyond experimental error) was observed after adding 0.04 mmol of base. After completing each titration, 0.1 ml of conc HCl was added and regeneration of the original spectrum of 6 was observed; uv-visible spectrum for the dianion of 5a, $\lambda_{max}$(-methanol) 347 nm (log ε 4.31), 418 (4.59), 445(4.63); the dianion of 5b, $\lambda_{max}$ (methanol) 228 nm(sh) (log ε 4.38), 265(4.25), 300(4.19), 350(4.31), 413(4.64); the dianion of 5c, $\lambda_{max}$ (methanol) 262 nm (log ε 4.30), 300(4.23), 401(4.69); the dianion of 5d, $\lambda_{max}$ (methanol) 264 nm (log ε 4.02), 300(4.16), 417(4.81); the dianion of 5e, $\lambda_{max}$ (methanol) 230 nm (log ε 4.29), 250(4.33), 301(4.22), 406(4.69); the dianion of 5f, $\lambda_{max}$(methanol) 228 nm (log ε 4.61), 286(4.21), 298(4.28), 326(4.24), 413 (4.83 ).

ANION RADICALS OF 5 EXAMINED BY ESR

Electrolytic reduction was carried out for the compounds 5a–5f by the following general procedures. About 3 mg of tetrabutylammonium perchlorate and 1 mg of 5 were placed in an electrolytic esr cell. A small piece of glass wool was placed between platinum wire electrodes to slow diffusion. After degassing, dry tetrahydrofuran (distilled from LiAlH$_4$, stored over Na-K anthracene) was vacuum-distilled into the cell. After three freeze-degas-thaw cycles the cell was sealed and placed in the esr cavity and a minimal current was passed through the cell to generate the esr signal. Coupling constants and g-values were measured using double-cavity technique with Fremmy's salt (potassium nitrosyldisulfonate, g = 2.0057) as reference (Table 2). For 5b an equally-spaced pattern of six (or possibly eight) lines was observed, with splitting of 0.75 G, line width 0.35 G, and g =2.0053. The relative intensities were approximately 1:5:5:5:3:1.

CYCLIC VOLTAMMETRY

A Princeton Applied Research Model 170 electrochemistry system was used with a three-electrode cell, having platinum-wire working and auxiliary electrodes and a saturated calomel reference electrode. All sample solutions were 1 mM in quinoid compounds with 0.1 M tetrabutylammonium perchlorate as a supporting electrolyte in dichloromethane which had been dried and distilled over $P_2O_5$. For all of compounds 5, each wave fulfilled the reversibility criteria for the electrode process:[22] the ratio of cathodic and anodic peak currents, $i_{pc}/i_{pa}$, becomes close to unity as the scan rqte is decreased, and a plot or peak current against square root of the scan rate is linear passing through the origin for both cathodic and anodic peaks in each case. For both waves in all the compounds, the separation between cathodic and anodic peaks decreased with slower scan rate reaching the minimal values of 0.08~0.1V, indicating the electron transfer is somewhat slower than the completely reversible case with fast electron transfer.[23] From this dependence of the peak separation upon scan rates, the electron transfer rate ($k_s$) at the platinum-wire electrode surface was calculated to be roughly 5 × 10$^{-3}$ cm/sec for all the compounds 5 using relationship reported by Nicholson.[24] The detailed cyclic voltammetric data are available as microfilm on request.

BIBLIOGRAPHY

1. R. West and D. C. Zecher, *J. Amer. Chem. Soc.*, 92, 155 (1970)
3. R. West, D. C. Zecher, S. K. Koster and D. Eggerding, J. Org. Chem., 40, 2295 (1975)
16. E. R. Altwicker, *Chem. Rev.*, 67, 475 (1967)
21. A Roedig and L. Horning, *Chem. Ber.*, 88, 2203 (1955)
22. R. Adams, "Electrochemistry at Solid Electrodes", M. Dekker, New York, N. Y., 1969; R. Nicholson and I. Shain, *Anal. Chem.*, 36, 706 (1964)
23. For a typical completely reversible case, the peak separation is expected to be 0.058V independent on the scan rate (see ref. 22)
24. R. Nicholson, *Anal. Chem.*, 37, 1351 (1965)

Table 1

| Uv-visible and Reflectrance Spectra of Alkylidenediquinocyclopropanes (5) | |
|---|---|
| Cmpd. | Uv-visible ($C_6H_6$) $\lambda_{max}$, nm (log ξ) | Reflectance $\lambda_{max}$, nm |
| 5a | 609(4.80), 640(sh)(4.25) | 510, 715, 870 |
| 5b | 591(4.82), 609(4.80) | 500, 670 |
| 5c | 608(4.70) | 560, 620, 925 |
| 5d | 672(4.60) | 400, 650 |

Table 1-continued

Uv-visible and Reflectrance Spectra of Alkylidenediquinocyclopropanes (5)

| Cmpd. | Uv-visible ($C_6H_6$) $\lambda_{max}$, nm (log $\xi$) | Reflectance $\lambda_{max}$, nm |
|---|---|---|
| 5e | 600(4.77), 621(4.75) | 525, 625, 655 |
| 5f | 610(4.84), 627(sh)(4.80) 668(sh)(4.34) | 590, 645 |

Table 2

Calculated and Observed Hyperfine Splitting Constants (Gauss) and g-Values for Anion Radicals

| Anion radical | Spin Density p calcd | $a_H$ calcd[a] | obsd | g-value |
|---|---|---|---|---|
| 5c | −0.0254 | 0.76 | 0.77 | 2.0053 |
| 5d | −0.0249 | 0.75 | 0.85 | 2.0052 |
| 5e | −0.0193 | 0.58 | 0.69 | 2.0054 |
| 5f | −0.0220 | 0.66 | 0.74 | 2.0054 |
| 1 | −0.014[b] | 0.42 | 0.43[b] | 2.0043[c] |
| 3 | −0.024[b] | 0.72 | 0.63[b] | 2.0046[b] |

$a_H$ = pQ with Q = −30G.
[b] Ref. 3

We claim:

1. An alkylidenediquinocyclopropane having the general formula

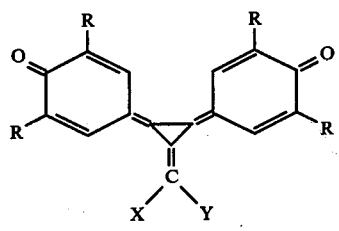

in which X and Y, when identifying separate groups, are selected from the group consisting of (a) NC (b) COOR

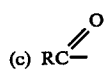
(c) RC— and, when identifying a single group, is selected from the group consisting of

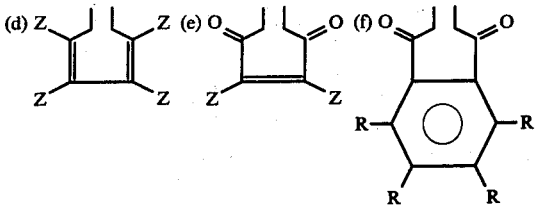

in which Z is a halogen group and in which R is a group selected from the group consisting of hydrogen, $C_1$-$C_{18}$ alkyl, cycloalkyl aryl and alkaryl.

2. An alkylidenediquinocyclopropane as claimed in claim 1 in which X and Y are both NC.

3. An alkylidenediquinocyclopropane as claimed in claim 1 in which X is NC and Y is $COOC_2H_5$.

4. An alkylidenediquinocyclopropane as claimed in claim 1 in which X and Y is a single group

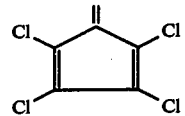

5. An alkylidenediquinocyclopropane as claimed in claim 1 in which X and Y is a single group

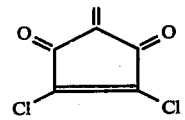

6. An alkylidenediquinocyclopropane as claimed in claim 1 in which the compound is 1,2-Bis(3,5-di-tert-butyl-4-oxo-2,5-cyclohexadiene-1-ylidene)-3-dicyanomethylenecyclopropane.

7. An alkylidenediquinocyclopropane as claimed in claim 1 in which the compound is 1,2-Bis(3,5-di-tert-butyl-4-oxo-2,5-cyclohexadien-1-ylidene-3-carboethoxycyanomethylenecyclopropane.

8. An alkylidenediquinocyclopropane as claimed in claim 1 in which the compound is 1,2-Bis(3,5-di-tert-butyl-4-oxo-2,5-cyclohexadien-1-ylidene)-3-diacetylmethylenecyclopropane.

9. An alkylidenediquinocyclopropane as claimed in claim 1 in which the compound is 1,2-Bis(3,5-di-tert-butyl-4-oxo-2,5-cyclohexadien-1-ylidene)-3-(2′,3′,4′,5′-tetrachloro-2′,4′-cyclopentadien-1′-ylidene)cyclopropane.

10. An alkylidenediquinocyclopropane as claimed in claim 1 in which the compound is 1,2-Bis(3,5-di-tert-butyl-4-oxo-2,5-cyclohexadien-1-ylidene)-3-(3′,4′-dichloro-3′-cyclopenten-2′,5′-dion-1′-ylidene)cyclopropane.

11. An alkylidenediquinocyclopropane as claimed in claim 1 in which the compound is 1,2-Bis(3,5-di-tert-butyl-4-oxo-2,5-cyclohexadien-1-ylidene)-3-(indene-1′,3′-dion-2′-ylidene) cyclopropane.

* * * * *

UNITED STATES PATENT AND TRADEMARK OFFICE
CERTIFICATE OF CORRECTION

PATENT NO. : 4,133,821

DATED : January 9, 1979

INVENTOR(S) : Robert C. West et al.

It is certified that error appears in the above-identified patent and that said Letters Patent are hereby corrected as shown below:

Column 6, line 44, "mnr" should read -- nmr --.

Column 8, line 60, before "-ylidene)" delete "140"

Signed and Sealed this

Twenty-ninth Day of May 1979

[SEAL]

Attest:

RUTH C. MASON
Attesting Officer

DONALD W. BANNER
Commissioner of Patents and Trademarks